(12) United States Patent
Hanna

(10) Patent No.: US 6,749,634 B2
(45) Date of Patent: Jun. 15, 2004

(54) INTRAOCULAR IMPLANT AND AN ARTIFICIAL LENS DEVICE

(75) Inventor: Khalil Hanna, Paris (FR)

(73) Assignee: Humanoptics AG, Erlangen (DE)

(*) Notice: Subject to any disclaimer, the term of this patent is extended or adjusted under 35 U.S.C. 154(b) by 0 days.

(21) Appl. No.: 09/958,943

(22) PCT Filed: Feb. 13, 2001

(86) PCT No.: PCT/FR01/00407
§ 371 (c)(1),
(2), (4) Date: Oct. 16, 2001

(87) PCT Pub. No.: WO01/60286
PCT Pub. Date: Aug. 23, 2001

(65) Prior Publication Data
US 2002/0138140 A1 Sep. 26, 2002

(30) Foreign Application Priority Data
Feb. 16, 2000 (FR) .......................................... 00 01884

(51) Int. Cl.⁷ ................................................. A61F 2/16
(52) U.S. Cl. .................... 623/6.37; 623/6.41; 623/6.39; 623/6.49
(58) Field of Search ...................... 623/6.37, 6.39–6.41, 623/6.44, 6.47, 6.49, 6.22

(56) References Cited

U.S. PATENT DOCUMENTS 6,485,516 B2 * 11/2002 Boehm ...................... 623/6.49

FOREIGN PATENT DOCUMENTS

| FR | 2 778 093 | 11/1999 |
|---|---|---|
| WO | WO 99/03427 | 1/1999 |
| WO | WO 99/29266 | 6/1999 |

* cited by examiner

Primary Examiner—David H. Willse
(74) Attorney, Agent, or Firm—Young & Thompson

(57) ABSTRACT

An accommodating intraocular implant for locating in the capsular bag, the implant comprising a single piece of elastically deformable material constituting a central lens (1) and at least two haptic portions (2, 4) in the form of radial arms for bearing via their free ends against the equatorial zone of the capsular bag, the free end of each radial arm (2, 4) being fitted with a shoe (6, 7) of substantially toroidal outside surface enabling the implant to bear against the equatorial zone of the bag, the connection between each shoe (6, 7) and the corresponding arm (2, 4) being of the hinge type situated in the vicinity of the posterior edge of the shoe (6, 7) and being formed by a first thin portion (2d, 4d) of the arm, while the connection between each arm and the lens is of the hinge type implemented at the anterior surface of the lens by a second likewise thin portion (2c, 4c) of the arm, the plane ($P_1$) containing the first thin portions being situated behind the plane ($P_2$) containing the second thin portions.

16 Claims, 9 Drawing Sheets

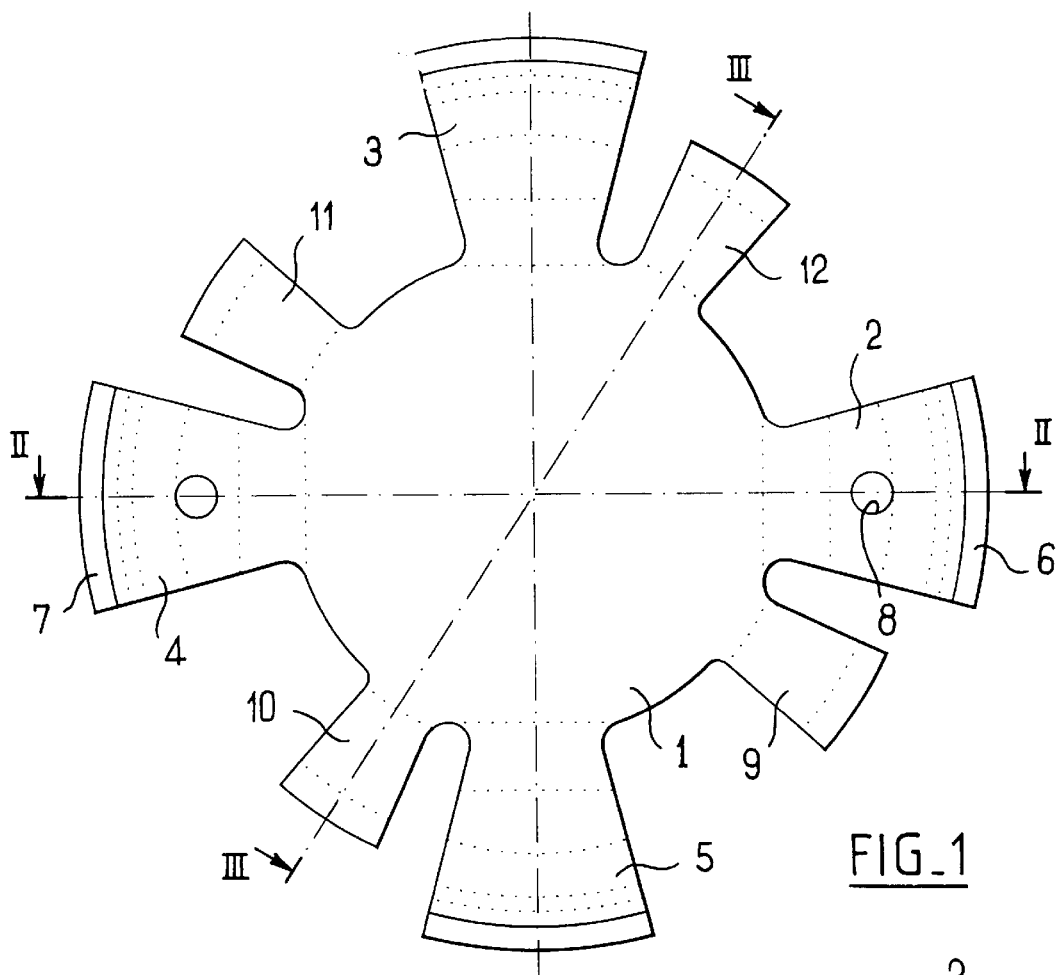
FIG_1
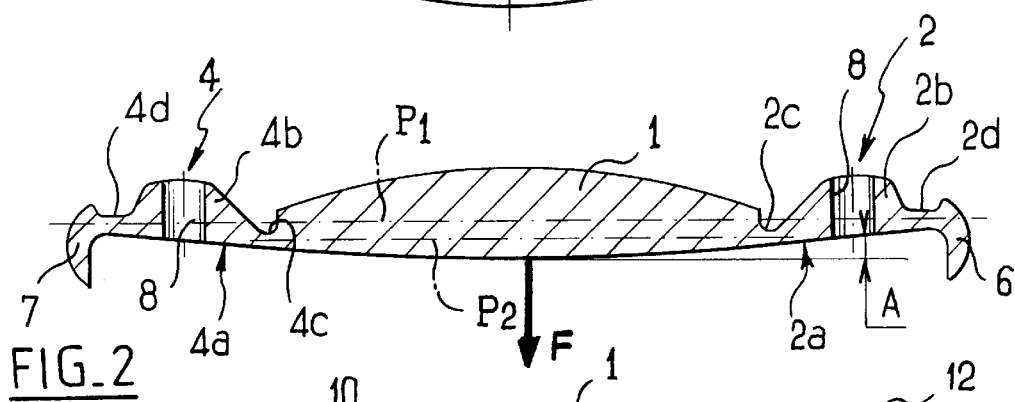
FIG_2
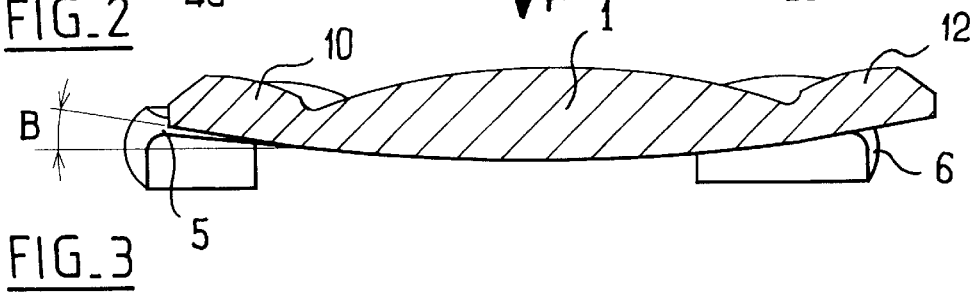
FIG_3

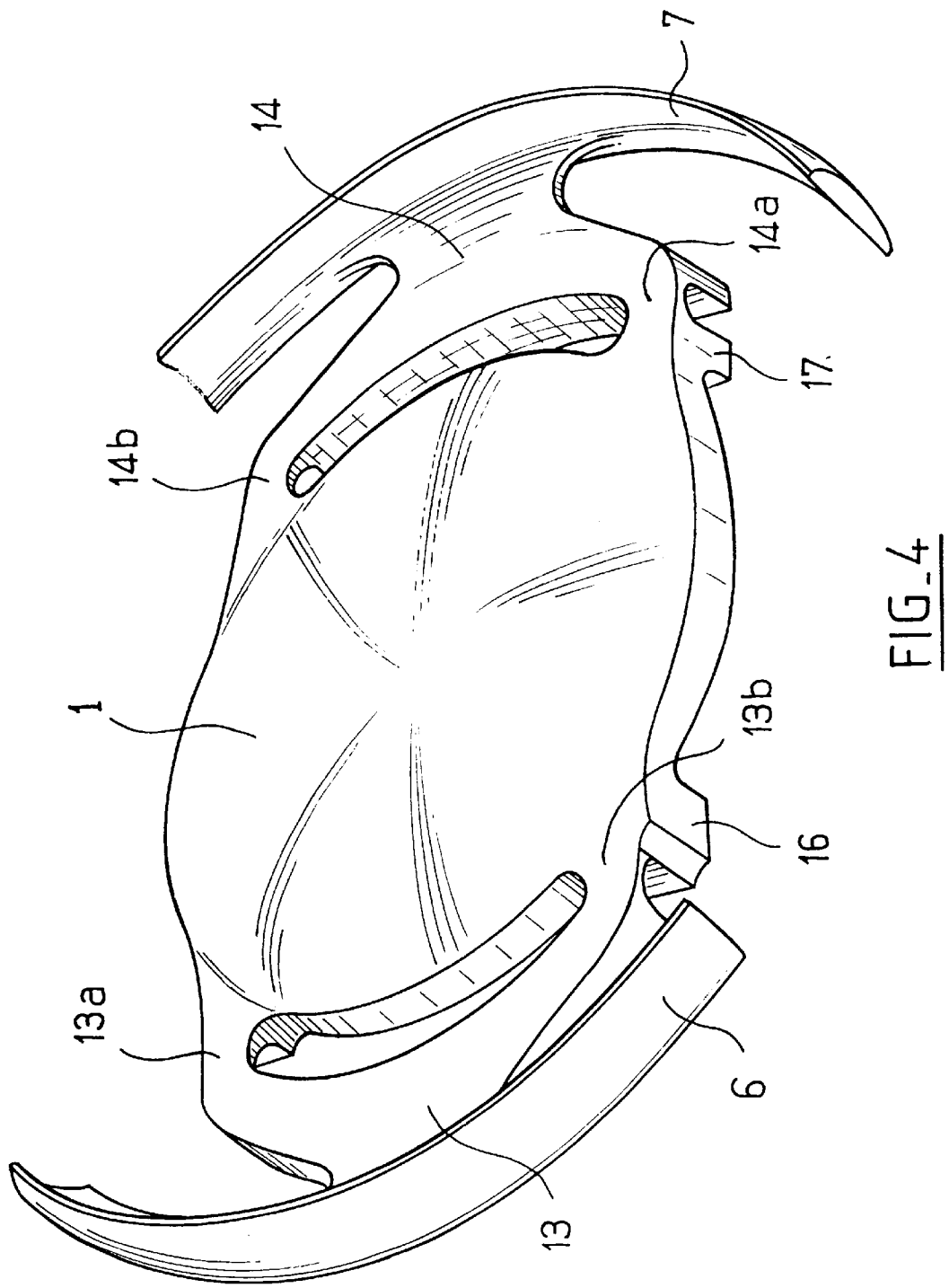
FIG_4

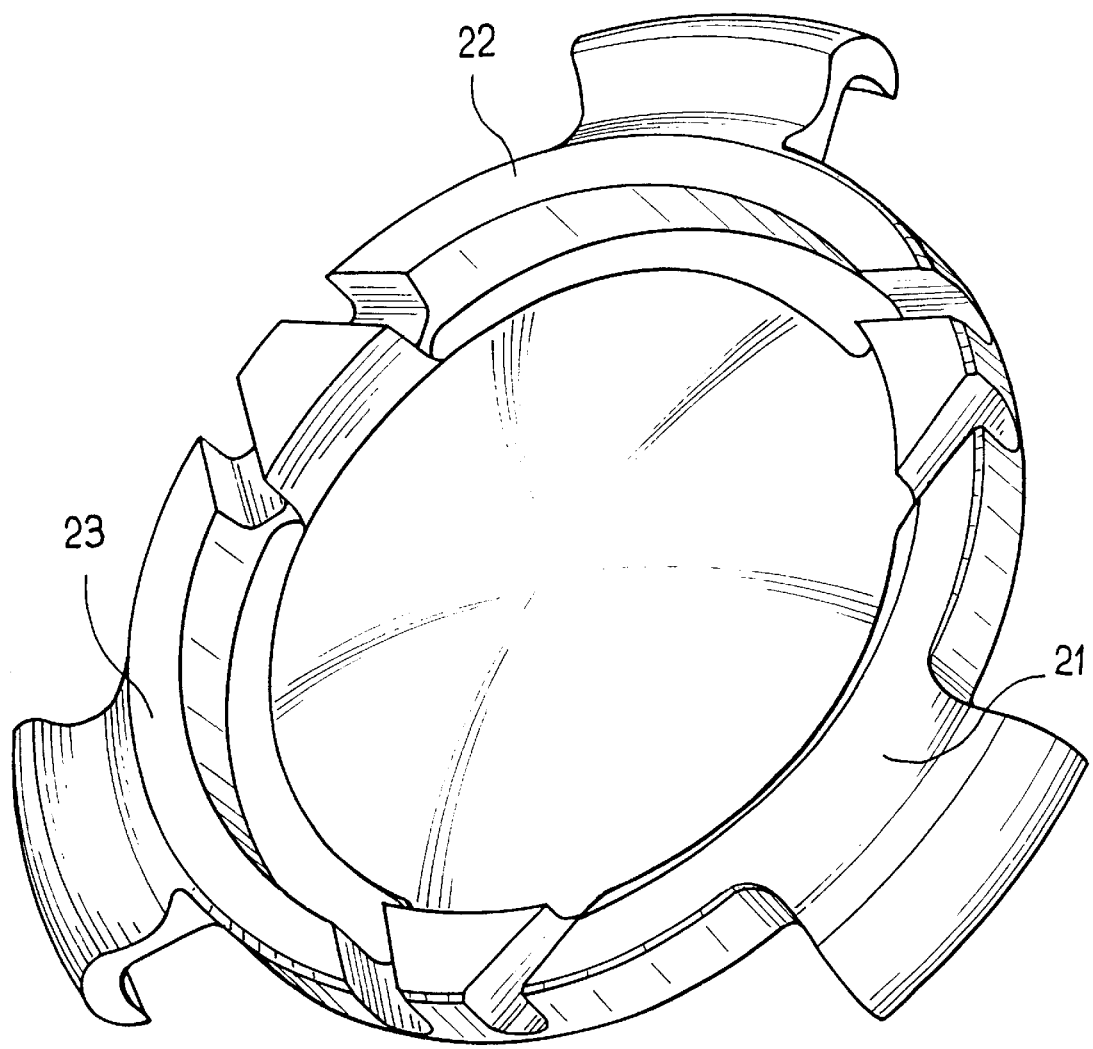
FIG_6

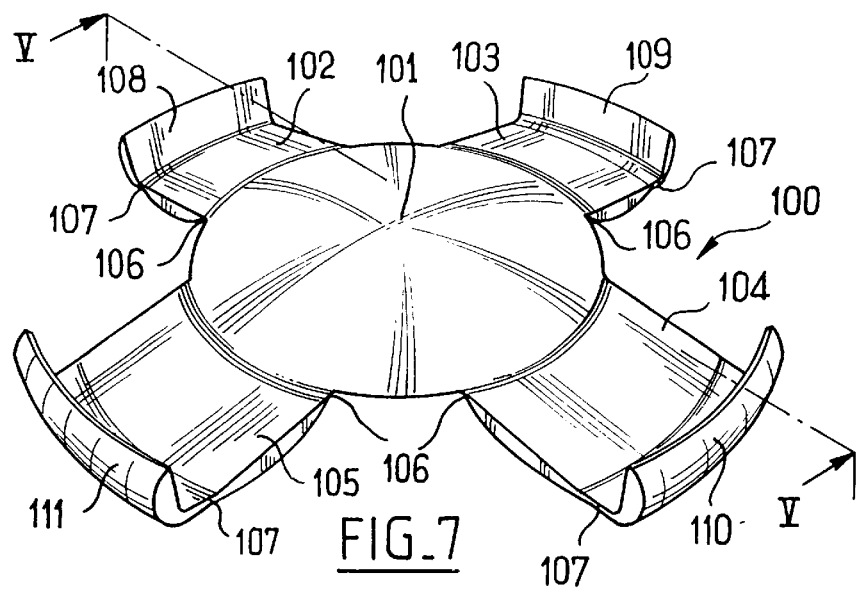
FIG_7
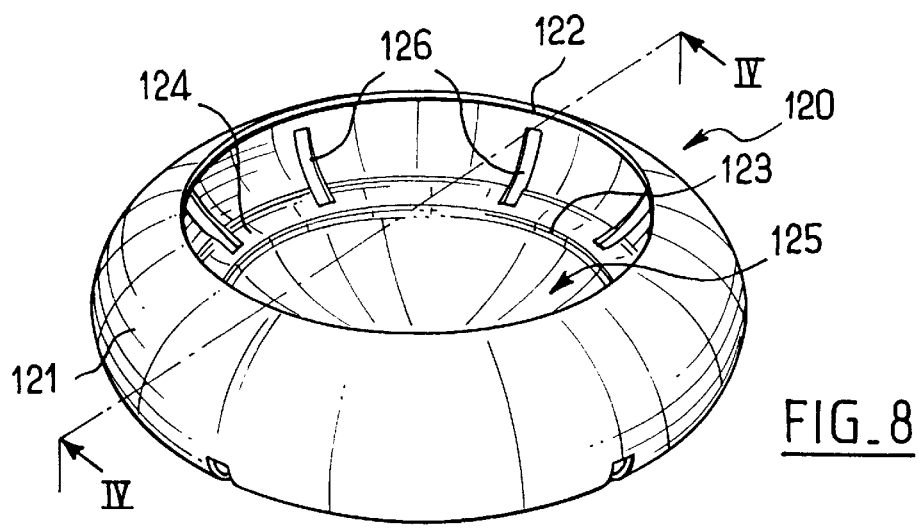
FIG_8
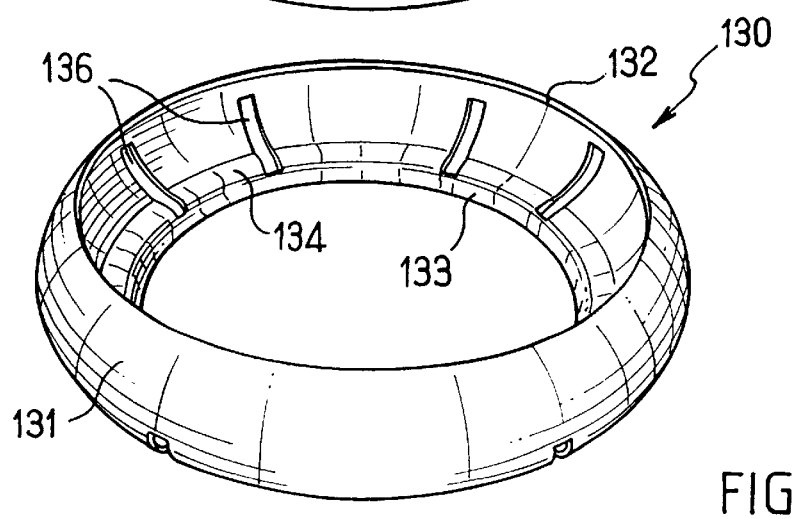
FIG_9

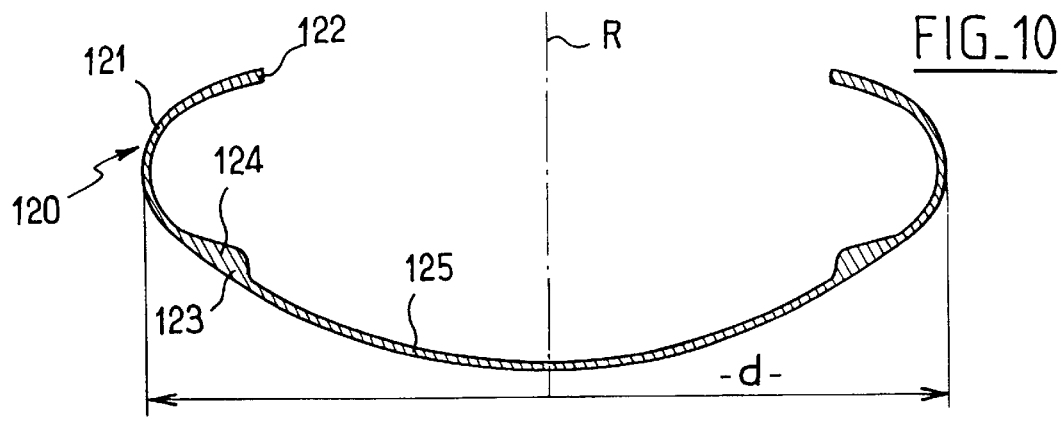
FIG_10
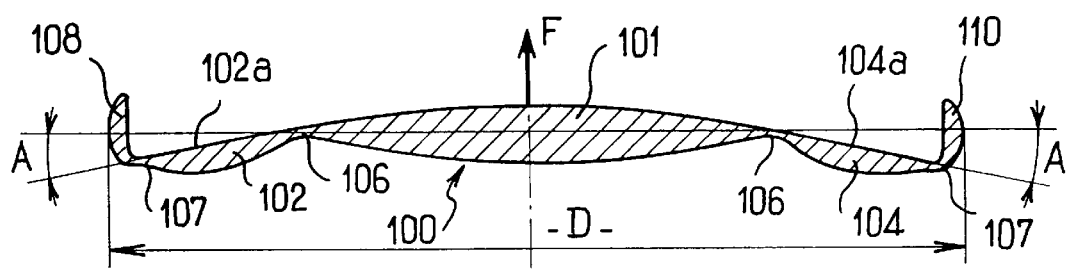
FIG_11
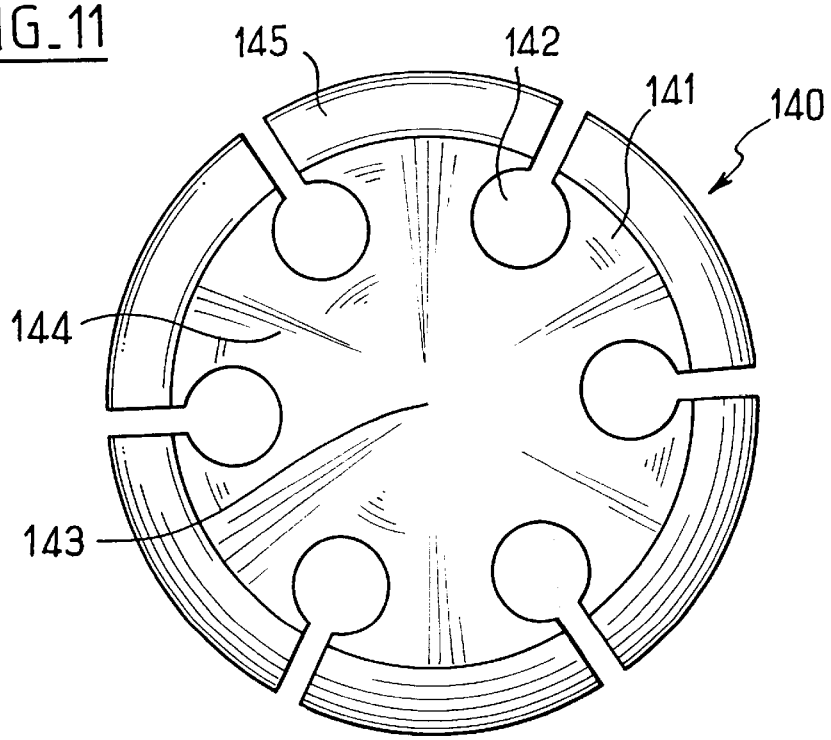
FIG_14

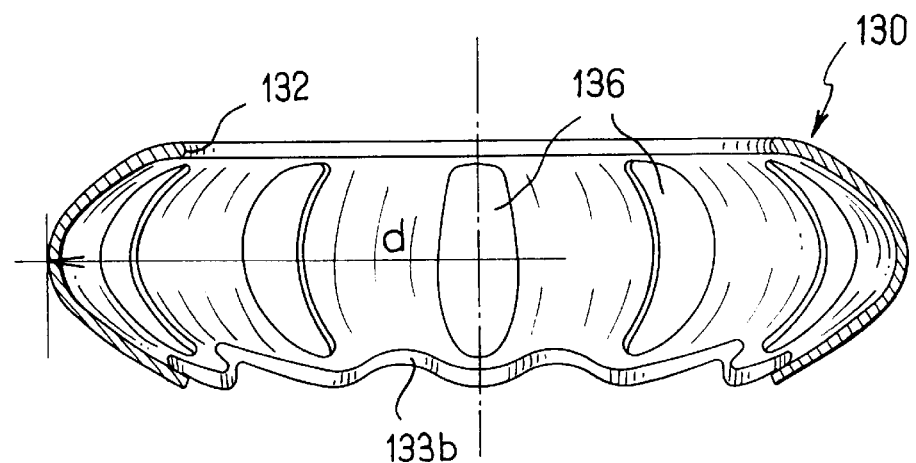
FIG_12
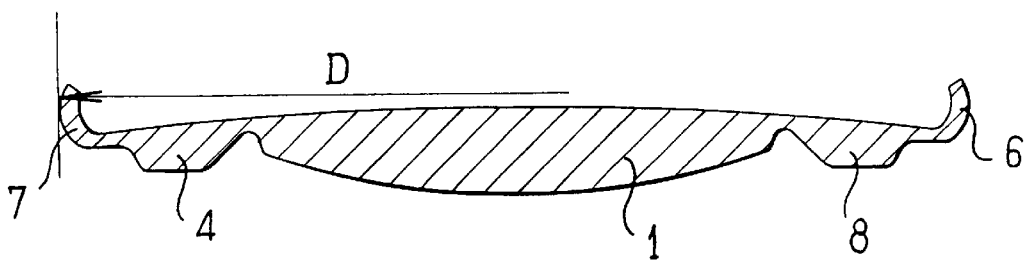
FIG_13
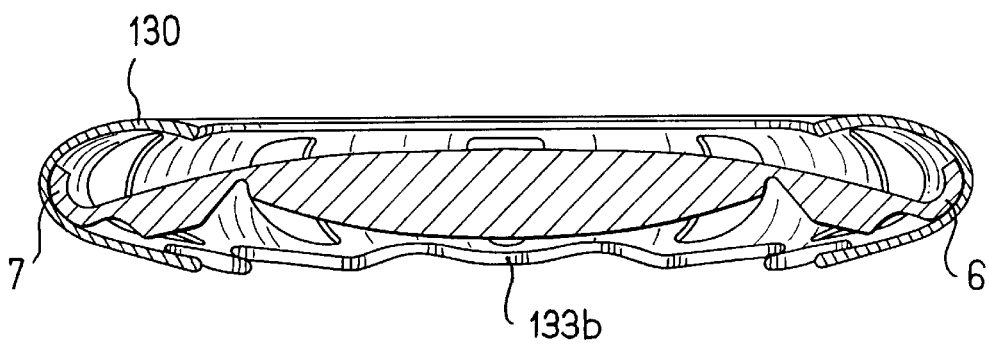
FIG_19

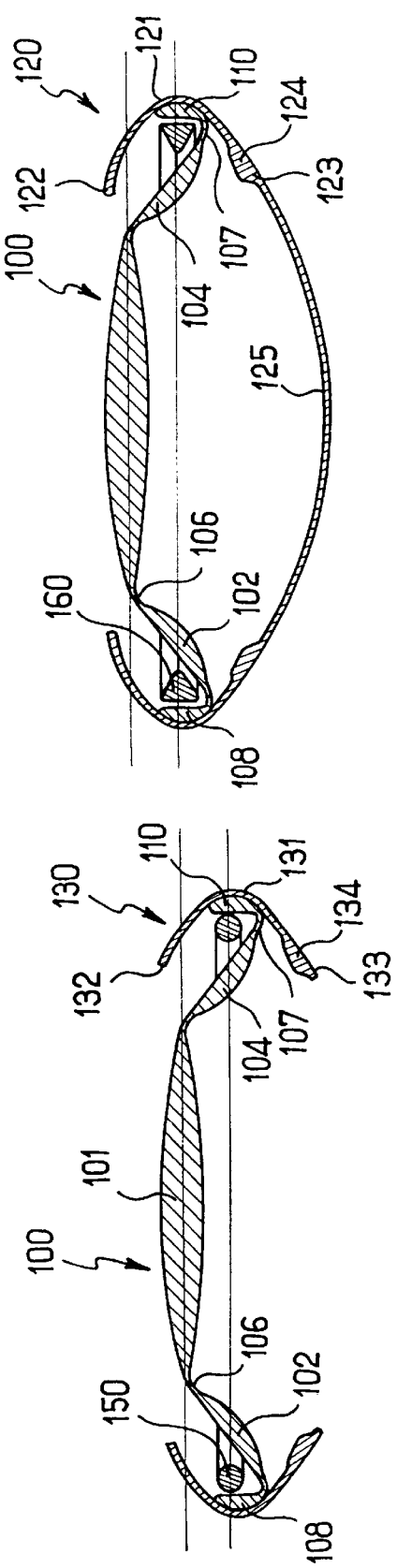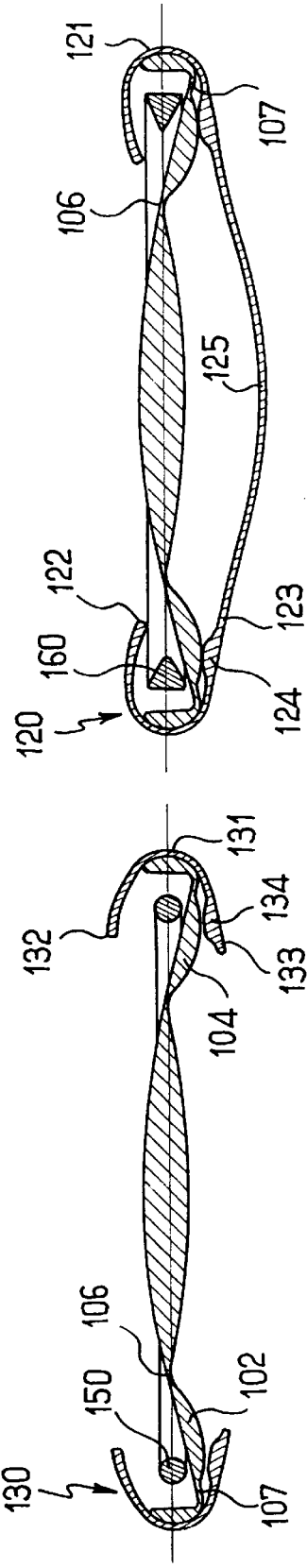

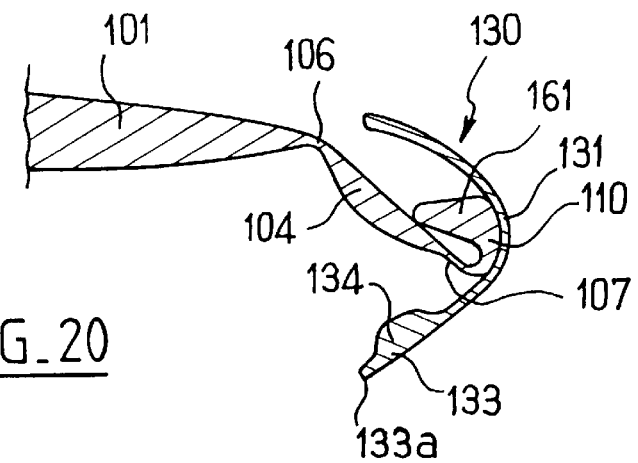
FIG_20
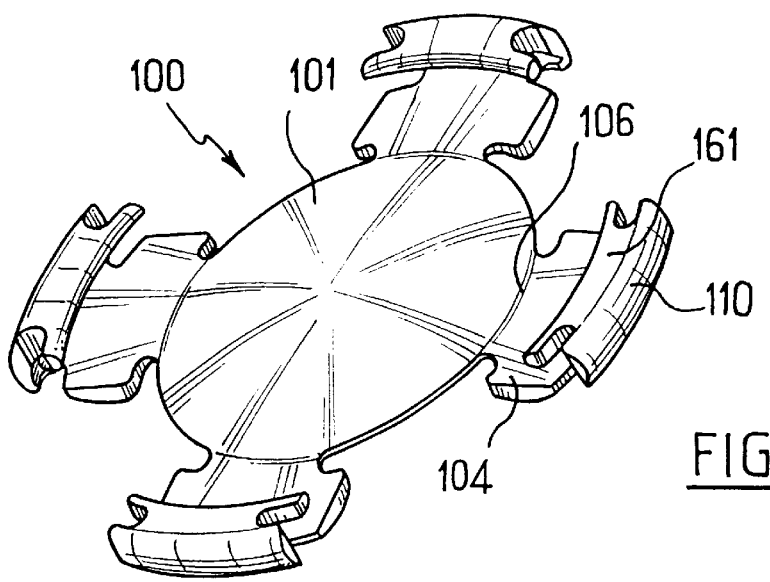
FIG_21
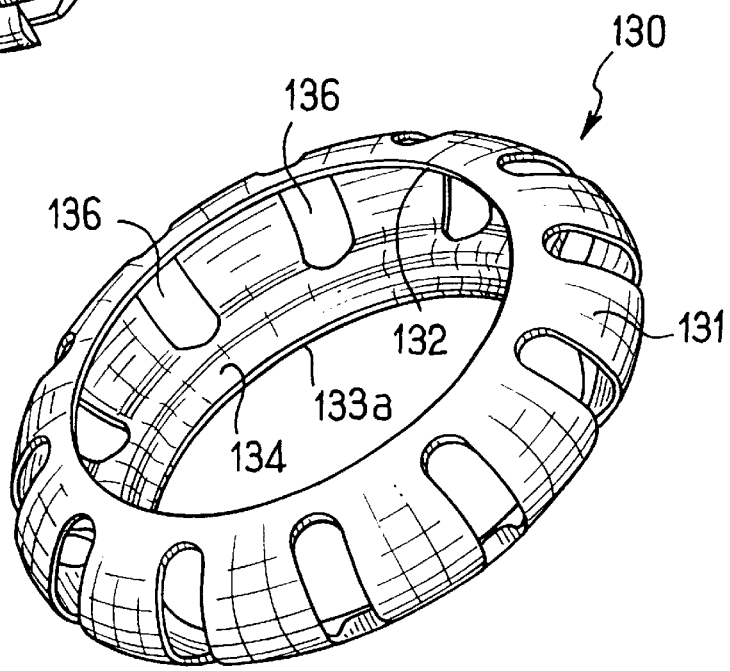
FIG_22

INTRAOCULAR IMPLANT AND AN ARTIFICIAL LENS DEVICE

The present invention relates to the field of intraocular implants, and more precisely to the field of lenses that are implanted after cataract surgery consisting in removing the natural lens from the capsular bag through a central and anterior capsulotomy (capsulorexis) having a diameter of 5 millimeters (mm) to 6 mm. As a result, the posterior and equatorial portions of the capsular bag are preserved.

BACKGROUND OF THE INVENTION

Replacing the natural lens with an implant has become an operation that is commonplace in the field of cataract surgery.

Until now, the implants used have not had the ability to restore any faculty of accommodation to an operated patient. It is known that the loss of accommodation which leads to presbyopia stems not from loss of function in the ciliary muscle and the associated zonular fibers, but firstly from a hardening of the lens material contained in the capsular bag, and secondly from an increase in the dimensions of the lens due to the patient aging. Hardening of the lens material opposes any modification being made to its shape by the capsular bag when the capsular bag is relaxed by the zonular fibers (near vision). The increase in the size of the lens has the consequence that only a fraction of the amplitude in the variation of the dimension of the ciliary muscle is transmitted to the capsular bag, since during muscle relaxation, a portion of this amplitude is used up in tensioning the zonular fibers before beginning to cause the outward displacement that generates a modification in the shape of the lens.

With a young subject, the lens material on its own, i.e. when not enclosed in the capsular bag, has approximately the shape taken up by the lens when in the de-accommodated state (far vision). This is the state in which the lens material tends to harden with age. Still with a young subject, the rest shape of the lens, i.e. of the lens material in the capsular bag and in the absence of any connection with the zonular fibers, is close to that of the accommodated state (near vision). In other words, the elasticity of the capsular bag constrains the lens material to leave its own rest state and take up an accommodated shape. Hardening opposes this molding of the lens material by the capsular bag.

Likewise, with a young subject and in the accommodated state of the eye, the axial zonular fibers are always tensioned without slack. This enables them to transmit the amplitude of ciliary muscle deformation to the capsular bag in full. The increase in the size of the lens causes the axial zonular fibers to be relaxed when the ciliary muscle is contracted, so relaxation of the muscle has an effect on the capsular bag only over a fraction of its stroke, with the first portion of this increase in diameter having the sole effect of retensioning the axial zonular fibers so as to cause them to take up a position in which they are able to drive the capsular bag over a second portion of the increase in diameter of the ciliary muscle.

Thus, when cataract surgery fully conserves both the posterior portion of the capsular bag and its equatorial portion, and leaves a peripheral fraction of its anterior wall in place as well, the conditions are such that accommodation is capable of being recovered. The full capacity of the capsular bag for elastic deformation is recovered; in the absence of any lens material, the bag shrinks elastically and the zonular fibers are again under tension. It is then possible to take advantage of the still-functioning "drive assembly" constituted by the ciliary muscle, the zonular fibers, and the remaining portions of the capsular bag.

Numerous implants have been designed that attempt to make use of contraction and relaxation of the ciliary muscle in order to modify the optical power of the eye. Implants are known comprising two pieces, a case received in the capsular bag and an optical portion inside the case. The case is supposed to track the shape of the capsular bag. As a result, at least in theory, the optical piece is caused to move along the optical axis of the eye, thus varying the optical power of the eye and thus providing vision accommodation. In this respect, mention can be made of document EP 0 337 390. It would appear that that implant provides poor performance since the mechanism for compressing the case produces only a very small amount of movement in the optical portion, so the faculty of accommodation is practically non-existent.

One-piece implants are also known comprising an optical central portion and a haptic portion (e.g. two radial arms extending from the periphery of the optical portion) having the function of being held captive in the collapsed equatorial zone of the capsular bag and by the formation of fibrosis. After the implant has been put into place between the collapsed membrane portions, the operating method then consists in maintaining the ciliary muscle in the relaxed state for the time required (a few weeks) to allow fibrosis to take hold of the ends of the haptic portions. During this time, the remainder of the anterior portion of the capsular bag shrinks, thus tending to stress the haptic portions towards the posterior portion of the bag and thus to press the optical portion against this posterior portion. At the end of fibrosis growth, the ciliary muscle is returned to normal control by the brain. Thus, when it contracts for near vision, the capsular bag is released, and the fibrosis zone tends firstly to tilt forwards with help from an increase in the internal pressure of the eye, and secondly to tighten radially, thereby causing the optical portion to move forwards, the radial shrinkage being transformed by the hinged or flexible haptic arms into a movement tending to cause the optical portion to protrude forwards. To accomplish this movement and the opposite movement when the ciliary muscle relaxes, the haptic portions are hinged to the edge of the optical portion or they are very flexible so as to be capable of moving or bending in front of and behind the mean plane thereof, in front for far vision and behind for near vision. In addition, the haptic portions slide in their sockets in the fibrosis tissue which has been generated between the collapsed portions of the capsular bag in the vicinity of its equator. That type of implant is described in document U.S. Pat. No. 5,674,282, for example.

In that device, the fibrosis tissue whose growth is encouraged is a factor which contributes to modifying interaction between the zonular fibers and the capsular bag and which makes it impossible to predict the final behavior of the implant during accommodation.

Finally, proposals have been made for another one-piece accommodating implant comprising an annular portion whose section is gutter-shaped and intended for being received in the equatorial zone of the capsular bag and from which there project arms connecting it to a central optical portion. Variation in the diameter of the equatorial zone of the bag towards and away from the center gives rise to radial thrust or traction on the arms, thereby causing the optical portion to move along the optical axis (see WO 99/03427).

In that device, the presence of the continuous outer annular portion constitutes a brake on deformation of the equatorial zone of the bag, and that diminishes the effectiveness of the implant in providing accommodation.

OBJECTS AND SUMMARY OF THE INVENTION

Unlike known devices, the present invention makes it possible to retain as much as possible of the accommodation faculties still available in an eye that has been subjected to a cataract operation.

A first object of the present invention is to provide a one-piece implant, and a second object is to provide an artificial lens device which comprises the implant and an intermediate piece between the implant and the capsular bag.

In the present description, the terms "anterior" and "posterior" should be understood in their meanings as used in ophthalmology, i.e. so far as the lens system is concerned, "anterior" is closer to the cornea, and "posterior" is further from the cornea. In the description below, these two adjectives are used even for devices that have not been implanted, with the description being as though they were implanted.

Thus, the implant of the invention is an accommodating intraocular implant for locating in the capsular bag, the implant comprising a single piece of elastically deformable material constituting a central lens and at least two haptic portions in the form of radial arms for bearing via their free ends against the equatorial zone of the capsular bag; the free end of each radial arm is fitted with a shoe of substantially toroidal outside surface enabling the implant to bear against the equatorial zone of the bag, the connection between each shoe and the corresponding arm being of the hinge type situated in the vicinity of the posterior edge of the shoe and being formed by a first thin portion of the arm, while the connection between each arm and the lens is of the hinge type implemented at the anterior surface of the lens by a second likewise thin portion of the arm, the plane containing the first thin portions being situated behind the plane containing the second thin portions.

Several advantages result from this structure. Firstly, any movement tending to bring the shoes towards the center of the lens causes the lens to move forwards, which corresponds to contraction of the ciliary muscle for near vision.

This forward movement is made that much more meaningful when:

the shoes transmit the reduction in capsular bag diameter in full, unlike an equatorial ring which always provides a certain amount of resistance to radial contraction that needs to be overcome; and the shoes reduce considerably the production of fibrosis tissue which would otherwise form a mass at the equator of the capsular bag that modifies the characteristics of the bag (towards less deformability), and thus its ability to respond over the greatest possible amplitude to variations in the tension of the zonular fibers. In this respect, it is preferable for the shoes to be quite long circumferentially, specifically for the purpose of opposing fibrosis growth (at least one-third of the circumference of the bag).

Preferably, the arms possess respective posterior projections so that in the most radially relaxed state, these projections bear against the posterior wall of the capsular bag and prevent the hinge planes from inverting, since that would prevent any accommodation.

Also preferably, each arm is in the form of an arch with the foot of each arch being connected to the lens via a thinned portion. It will be understood that by means of this shape, the working length of each haptic arm can be lengthened, and thus for given radial contraction greater amplitude can be obtained in the forward movement of the lens. The arm of maximum possible working length is an arm which is hinged to the lens at the ends of a diameter which extends perpendicularly to the middle radius of the arm. However, under such conditions the connection between the arm and the lens would be concentrated at the two ends of said diameter and that would make the orientation of the lens unstable. That is why a preferred embodiment is in the form of an implant having three haptic arms distributed at 120° intervals around the lens.

In this respect, it should be observed that in order to obtain maximum movement of the lens, it is necessary to ensure that the gap between the anterior and posterior planes containing the two types of hinge is as small as possible in order to take advantage of the region of maximum variation in the sinewave function which governs the transmission of these movements.

Furthermore, the implant of the invention advantageously includes, between pairs of haptic arms, rigid radial extensions rooted in the periphery of the lens and forming abutments opposing expulsion of the implant from the capsular bag by coming into contact with the remaining portion of the anterior wall of the bag around the central opening that has been made therein. These extensions are located outside the bisectors of the angles between pairs of haptic arms so that the implant remains easy to fold along certain diameters thereof which have neither arms nor extensions.

When the arms are in the form of arches, the hinge connection between the lens and each foot of an arm takes place via these radial extensions, just outside the maximum diameter of the lens.

The invention also provides an artificial lens device which comprises, in addition to the above-described implant, an intermediate element that is elastically deformable, in particular in the radial direction, and that is designed to cover the interior face of the capsular bag or at least the equatorial zone thereof. Thus, in addition to the implant, the device also comprises an element which is separate from the implant, and which is elastically deformable, with at least a peripheral portion in the form of a radially deformable gutter whose diameter at the bottom of the gutter, in the rest state, is less than the outside diameter of the implant, as measured on the outside face of each shoe when in the rest state.

The outer equatorial diameter of the intermediate element, while in its rest state, corresponds to the equatorial diameter that the accommodated lens used to have when the intended subject was 20 to 30 years old.

When the implant is put into place in the gutter, an equilibrium state is obtained for the assembly which is such that the outer equatorial diameter of the assembly is greater than that of the intermediate element on its own and such that the equatorial diameter of the implant is less than that which it has at rest. This equilibrium state is the state reached when the radial contraction forces of the gutter-shaped piece are equal to the radial expansion forces of the implant.

By computer-assisted design methods, it is possible with given mechanical characteristics (i.e. given materials) to determine the various critical dimensions and shapes for the implant and for the gutter, particularly concerning the hinges of the haptic arms of the implant and concerning the thickness of the equatorial portion of the gutter, which together condition such or such an equilibrium state and the amount of energy required to modify it. It is then possible to match the implant to the subject who receives it, thereby optimizing the ability of the subject to accommodate.

For example, if the capsulorexis of the anterior wall is small in size and if the amount of fibrosis tissue produced by the subject is assumed to be small, then a device should be put into place in the capsular bag for which the equilibrium state is close to the accommodated state which the subject's natural lens used to have when the subject was 25 or 30 years old. However, with capsulorexis of larger size and a tendency towards a large amount of fibrosis, the device to be put into place should have a rest state in which the implant takes up a position relative to the intermediate element that is close to far vision, with the outside dimension of the device still being that which the natural lens used to have in the de-accommodated state (in the absence of accommodation) when the subject was 25 to 30 years old.

After the device has been put into place in the capsular bag, the bag tends to contract elastically so as to come into contact with the element of the device which forms the case of the implant. Since the size of the case corresponds to the size the lens material used to have when the patient was young (25 to 30 years old), i.e. an age when the ability to accommodate is large, all of the components driving accommodation (and in particular the zonular fibers) are restored to their state of maximum efficiency as it existed at that time.

BRIEF DESCRIPTION OF THE DRAWINGS

Other characteristics and advantages will appear from the following description of various embodiments of the invention.

Reference is made to the accompanying drawings, in which:

FIG. 1 is a view of the anterior face of an implant of the invention;

FIG. 2 is a section view on line II—II of FIG. 1;

FIG. 3 is a section view on line III—III of FIG. 1;

FIGS. 4 and 5 are perspective views respectively from the anterior face and from the posterior face showing a variant embodiment of the FIG. 1 implant;

FIG. 6 is a perspective view from the posterior face of another variant embodiment of the implant of the invention;

FIG. 7 is a perspective view from above of another embodiment of the implant of the invention;

FIG. 8 is a perspective view of a first embodiment of the gutter piece of the artificial lens device of the invention;

FIG. 9 is a like view showing a variant embodiment of the gutter piece;

FIGS. 10 and 11 are sections respectively through the pieces of FIG. 8 and of FIG. 7 in planes IV—IV and V—V of these figures;

FIGS. 12 and 13 are like views showing a variant of the embodiment of FIGS. 10 and 11;

FIG. 14 is a plan view of another variant embodiment of the implant of the invention;

FIGS. 15 and 16 are diametral sections through the device of FIGS. 7 and 9, respectively in its near vision state and in its far vision state;

FIGS. 17 and 18 are views identical to those of FIGS. 15 and 16 for a device made using the pieces of FIGS. 7 and 8, shown respectively in the same states;

FIG. 19 is a section view through a device of FIGS. 12 and 13 in its equilibrium state close to a far vision state; and FIGS. 20, 21, and 22 show another variant embodiment of the device of the invention.

MORE DETAILED DESCRIPTION

Figure 5:
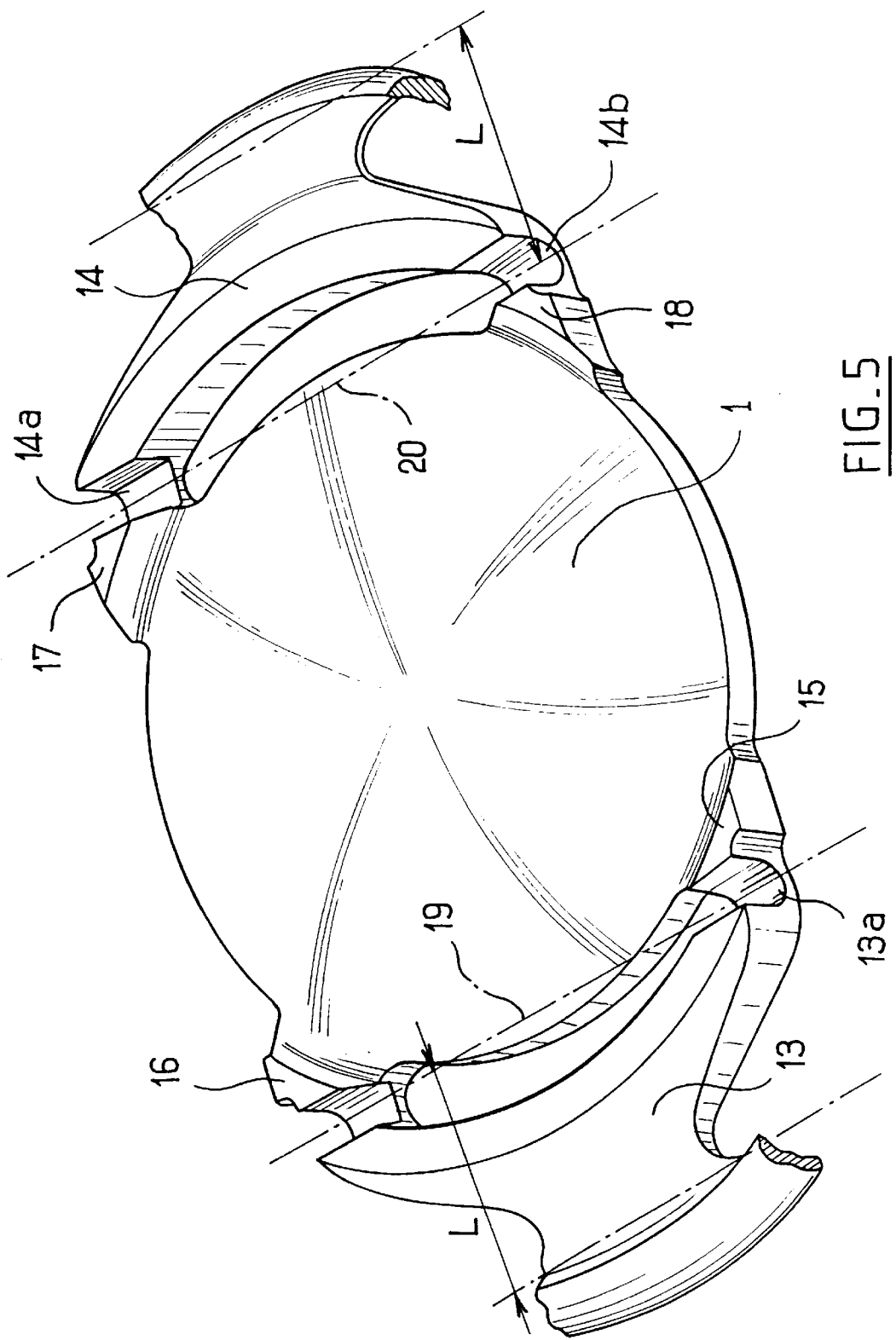

The material from which the various components of the implant of the invention are made is a material that is well known in the field in question, and is foldable acrylic, or silicone elastomer, for example. These materials are elastically deformable firstly to enable them to be folded up for inserting the implant into the capsular bag through an incision of small size made in the eye of the patient, and secondly to ensure they have shape memory enabling each of them to return to its rest shape.

The implant shown in FIGS. 1, 2, and 3 comprises a central lens 1, e.g. a biconvex lens having a diameter of about 5 mm to 6 mm. At the periphery of this central lens 1, the implant has four haptic arms 2, 3, 4, and 5 extending radially outwards and rearwards from the lens 1. As an indication, in order to illustrate this rearward inclination of the haptic arms, the anterior surface 2a, 4a of each arm forms together with the midplane of the lens an angle A lying in the range 2° to 15° (preferably 5°).

In FIGS. 2 and 3, it can be seen that each arm has a midsection 2b, 4b that bulges from its posterior face and that is situated between a thin portion 2c, 4c for connection to the periphery of the lens and a thin portion 2d, 4d for connecting the arm to a shoe 6, 7 which extends substantially perpendicularly to the general plane of the lens and whose outside surface is substantially toroidal. The shoe of each haptic arm extends for the most part to project from the anterior surface 2a, 4a of the corresponding arm. In other words, the thin connection zones 2d, 4d are close to the posterior edges of the shoe. The thin zones 2c, 2d, 4c, 4d are implemented as grooves in the posterior faces of the arms and the zones 2c, 4c are preferably thinner than the zones 2d, 4d (e.g. respectively 70 microns ($\mu$m) and 200 $\mu$m when the lens has a thickness of 1 mm and is made of a given acrylic material). At least one of the four haptic arms (two in the figures) is provided with an orifice 8 enabling the surgeon to manipulate the implant inside the capsular bag by means of a tool inserted into said orifice.

The thin portions 2c, 2d, 4c, 4d constitute the hinges between each arm and firstly the lens and secondly its shoe. The axis of rotation of each hinge is assumed to be situated approximately in the middle of the thickness of each zone. The plane $P_1$ containing each hinge of the type 2d, $4_d$ is situated behind the plane $P_2$ containing the hinges of the type 2c, 4d so that when radial compression is applied to the shoes it generates movement of the lens 1 in the direction given by arrow F.

Interposed between the haptic arms 2 to 5, the implant shown in the figures has radial extensions 9, 10, 11, 12 shown in section in FIG. 3. These rigid extensions constitute members that come into abutment against the remainder of the anterior wall of the capsular bag surrounding the opening made through said wall. In order to ensure that such abutment does not occur during movement corresponding to the normal accommodation phenomenon, the radial size of these extensions is less than that of the haptic arms and they extend so as to be inclined towards the posterior face of the implant at an angle B lying in the range 10° to 20°. Angularly, these extensions are not located on the bisectors of the angles formed between pairs of adjacent haptic arms. This characteristic serves to leave two zones in the vicinity of said bisectors that contain neither arms nor extensions, thereby making the implant easier to fold about diameters passing through said zones.

As shown in FIGS. 1 to 3, the combined angular extent of the haptic arms at their shoes occupies a total of about 120°. Larger values could be provided to improve the transmission of forces and to contain fibrosis tending to collapse the two walls of the capsular bag at its equator.

The variant embodiment of the implant shown in FIG. 4 (anterior face) and in FIG. 5 (posterior face) has two arch-shaped haptics fitted on the outside with respective shoes 6, 7 (shown in this figure), each of considerable angular extent (lying in the range 60° to 90°), and the haptics are connected to the lens via feet 13a, 13b, 14a, 14b each rooted in a respective triangular extension 15, 16, 17, 18, of triangular shape in this example, and constituting the abutments described above. Each of the feet 13a, 13b, 14a, and 14b is thinned by a respective groove, with the grooves common to a given arm having a common axis 19, 20 defining the hinge axis of the connection between the arm and the lens. It will be understood that by varying the positions of the feet 13a, 13b and 14a, 14b along the lens, it is possible to vary the working length L of each arm, i.e. the distance between the axes of the shoe-and-arm hinge and of the arm-and-lens hinge. A compromise needs to be found between having a long working length which contributes to a large amount of movement along the optical axis and ensuring that the lens is held stably by the arms.

Whereas in FIGS. 4 and 5 the feet of the arch-shaped arms are implanted at 90° from each other, in the variant shown in FIG. 6, the haptic arms 21, 22, and 23 are three in number with the feet of the arms being spaced apart by about 120°. Other things being equal, the working length of each arm in this variant is greater than in the variant of FIGS. 4 and 5.

The artificial lens device described with reference to FIGS. 7 to 19 comprises an implant which can be identical to that described above (or in the form shown in these figures) together with a separate element which covers at least the inside equatorial surface of the capsular bag.

As in the preceding figures, the implant 100 comprises a central lens 101, e.g. a biconvex lens having a diameter of about 5 mm to 6 mm and four haptic arms 102, 103, 104, and 105 extending radially outwards and rearwards from the lens 101 (the face visible in FIG. 7 is the front face of this piece).

Each arm possesses a bulging radial section between a thin portion 106 connecting it to the periphery of the lens 101 and a thin portion 107 connecting the arm to a respective shoe 108, 109, 110, 111 as in the preceding figures.

The portions 106 and 107 constitute resilient hinges of the arms, connecting each arm firstly to the central lens and secondly to the respective shoes. It should be observed that for given material, in such an implant designed to co-operate with a separate element, the thickness of the hinge-forming zones will generally be greater than that of the hinges in an implant for use on its own.

The implant is shown in FIGS. 7 and 11 in its rest state. The diameter of the implant in the rest state as measured from the outside surfaces of two opposite shoes is referenced D. As an indication, this dimension can lie in the range 9.5 mm to 10.5 mm.

The device of the invention also comprises an element that is separate from the implant and that is shown in a rest state in FIGS. 8 and 10, for a first embodiment, and in FIG. 9 for another embodiment. This element 120 carries a gutter-shaped portion 121 defined by an anterior lip 122 and a posterior lip 123 provided with an internal bead 124, the posterior lip 123 being extended as a dome 125 closing the posterior portion of this element 120. This gutter-shaped portion is provided with transverse slots 126 co-operating with its deformation ability both in the direction parallel to its axis of revolution R and in a direction perpendicular thereto.

The greatest diameter of the element 120, referenced d in FIG. 10 and referred to as its equatorial diameter, is substantially equal, at rest, to the diameter of the lens of a subject, and in particular the diameter which the lens used to have when the subject who is to be operated on was 25 to 30 years old, and as measured in the accommodated state, i.e. for near vision.

The variant 130 of the element 120 shown in FIG. 9 is identical thereto except that the dome 125 is not provided on the element 130. This element thus comprises merely a gutter 131 with lips 132, 133 and a bead 134 identical to the gutter portion 121 shown in FIGS. 8 and 10.

In the variant shown in FIGS. 12 and 13, the separate element is of the same type as the element 130 of FIG. 9, but the openings 136 are larger so as to give greater flexibility to deformation of the gutter, and the lower lip 133b does not have a bead but undulates in festoons. This element is adapted to receive an implant having the shape of the implant shown in FIGS. 1 and 3 and reproduced in FIG. 13. As in the case of FIGS. 10 and 11, it can be seen that the outside diameter d of the element 130 (and thus a fortiori its diameter in the bottom of the gutter) is less than the diameter D of the implant.

FIG. 14 is a plan view of a variant embodiment 140 of the implant 100 of FIG. 7. The difference between the two embodiments lies in the fact that in FIG. 14, the implant 140 has six haptic arms 141 separated from one another by gaps 142 that are keyhole-shaped. As in FIG. 7, these arms are connected to the central lens 143 by hinge zones 144 and to respective end shoes 145 likewise by hinge zones that are not visible in FIG. 14.

FIGS. 15 and 17 show the artificial lens device of the invention in its equilibrium state when the implant 100 is received in the case example 120, 130. The implant bears against the inside surface of the gutter by means of the substantially toroidal outside surfaces of the shoes which thus press closely against said inside surface. The implant exerts a force on the case element which tends to expand radially. However, the case element opposes this force with force that leads to a rest state in which the implant is much more highly deformed than is the case element. The equilibrium state of the device is thus its state for near vision (placed in the capsular bag when the ciliary muscle is contracted, the shape of the implant is close to said equilibrium state, the capsular bag then exerting practically no force on the case). The lens is thus projected forward of the equatorial plane of the element 120, 130.

When this device is placed in the capsular bag, relaxing the ciliary muscle tends to cause it to take up the state shown in FIGS. 16 and 18. Relaxation of the ciliary muscle puts the zonular fibers under tension so that, via the capsular bag, they stretch the element 120, 130 outwards by flattening the gutter, thus giving the implant 100 the ability to return towards its rest position and thus return the lens 101 to the vicinity of the equatorial plane of the element 120, 130. The limit for rearward movement of the lens is reached when the haptic arms come into contact with the bead 124, 134 carried by the posterior lip 123, 133 of the element 120, 130. In this respect, it will be observed that deformation of this element between FIGS. 15 and 17 and between FIGS. 16 and 18 lies not only in its equatorial diameter being extended radially, but also in the lips of the gutter portion being folded towards each other.

The function of the membrane forming the capsular bag is almost negligible on the case of the implant in terms of its ability to deform. Nevertheless, the capsular bag constitutes means for transmitting forces exerted by the zonular fibers. However, after the operation, there can be a danger of fibrosis developing on the inside face of the capsular bag, between the bag (which by definition is larger than the case of the implant) and the case of the implant. If this is to be expected clinically, it is preferable to implant a device of the kind shown in FIG. 19 in which the equilibrium state is close to the de-accommodated state of the eye (far vision). If the fibrosis takes on abnormal dimensions, the element 130 can become compressed, thereby tending to expel the implant from the capsular bag. To counter this tendency, the existence of the abutment described with reference to FIGS. 1 to 6 is recalled. Finally, a device of the invention can be provided in which the size D of the implant is exactly equal to the size d of the gutter element minus (twice) its thickness in the equatorial zone so that the equilibrium state of the implant in the gutter corresponds to the rest state both of the implant and of the gutter. Under such circumstances, the gutter is preferably deformable under very small forces and acts solely to line the inside of the capsular bag if it needs to be reinforced.

In another variant, the device of the invention includes a final piece constituted by a ring 150 of circular section in FIGS. 15 and 16, or 160 of triangular section in FIGS. 17 and 18, which ring is mounted to float inside the device so as to come into contact with the shoes of the haptic arms in order to provide vigorous opposition to any excessive radial contraction of the gutter element. It can thus be seen in FIGS. 15 and 17 that this ring 150, 160 has an outer circumference whose diameter is substantially equal to the diameter of the device in its equilibrium state as measured across the inside faces of the shoes of the haptic arms.

FIG. 20 is a fragmentary section view of a variant embodiment of the device as shown in FIG. 15. The difference between these embodiments lies firstly in the ring 150 being replaced by internal projections 161 from the shoe 110 to perform exactly the same function as the ring 150 (or 160 in FIG. 17), i.e. to oppose excessive radial contraction of the gutter. Secondly, this difference also lies in the shape of the end of the posterior lip 133 of the gutter element 130 which has a nib 133a constituting a barrier against cells of the capsular bag proliferating from its equatorial region towards the center of the bag.

FIGS. 21 and 22 are two perspective views of this variant embodiment of the invention in configurations similar to those shown respectively in FIGS. 7 and 10, with identical references being used for identical elements.

It will be understood that the device of the invention behaves like an elastic body capable of being deformed to a considerable extent under the effect of forces that are very small (of the order of $1\times10^{-5}$ newtons (N) to $2\times10^{-5}$ N). The forces that serve to deform it are merely additional forces produced by the ciliary muscle to disturb an equilibrium state between opposing forces developed by the implant against the case element and by the case element against the implant, and these forces are of a different order of magnitude.

What is claimed is:

1. An accommodating intraocular implant adapted to be located in a capsular bag, the implant comprising a single piece of elastically deformable material constituting a central lens (1) and at least two haptic portions (2, 4) in the form of radial arms for bearing via free ends of the radial arms against an equatorial zone of the capsular bag, wherein the free end of each radial arm (2, 4) is fitted with a shoe (6, 7) of substantially toroidal outside surface enabling the implant to bear against the equatorial zone of the bag, the connection between each shoe (6, 7) and the corresponding arm (2, 4) being of a hinge type situated in the vicinity of a posterior edge of the shoe (6, 7) and being formed by a first thin portion (2d, 4d) of the arm, while the connection between each said arm and the lens is of the hinge type implemented at an anterior surface of the lens by a second likewise thin portion (2c, 4c) of the arm, a plane ($P_1$) containing the first thin portions being situated behind a plane ($P_2$) containing the second thin portions, and including at least two rigid radial extensions (10, 12) extending from the lens (1) and interposed between pairs of the haptic arms, each extension being of radial length shorter than that of the arms and serving to enable the implant to come into abutment against edges of the opening in the capsular bag.

2. An implant according to claim 1, wherein between said hinge-forming thin portions, each arm (2, 4) has a posterior bulge (2b, 4b).

3. An implant according to claim 1, wherein each arm (13, 14) is in the form of an arch having feet (13a, 13b, 14a, 14b) connected to the lens (1) via thin zones oriented along a line (19, 20) perpendicular to a middle radius of the arm.

4. An implant according to claim 3, wherein each radial extension forms a common zone (15, 16, 17, 18) for connecting pairs of adjacent said feet of the two arch-shaped arms to the lens.

5. An implant according to claim 4, comprising three arms (21, 22, 23) in the form of arches regularly disposed around the lens (1).

6. An implant according to claim 1, wherein the abutment-extensions are situated away from bisectors of the angles between two consecutive said radial arms.

7. An implant according to claim 1, wherein the angular extent of contact between all of the shoes and the equatorial portion of the bag is not less than 120°.

8. An accommodating artificial lens device comprising an accommodating intraocular implant (100) comprising a single piece of elastically deformable material constituting a central lens (1) and at least two haptic portions (2, 4) in the form of radial arms, wherein a free end of each radial arm (2, 4) is fitted with a shoe (6, 7) of substantially toroidal outside surface, the connection between each shoe (6, 7) and the corresponding arm (2, 4) being of a hinge type situated in the vicinity of a posterior edge of the shoe (6, 7) and being formed by a first thin portion (2d, 4d) of the arm, while the connection between each said arm and the lens is of the hinge type implemented at an anterior surface of the lens by a second likewise thin portion (2c, 4c) of the arm, a plane ($P_1$) containing the first thin portions being situated behind a plane ($P_2$) containing the second thin portions, the accommodating artificial lens device further comprising an elastically deformable element (120, 130) separate from the implant, the element having at least a radially-deformable gutter-shaped peripheral portion whose diameter at a bottom of the gutter in a rest state is no greater than an outside diameter of the implant measured across outside faces of the shoe (110) when the implant is in the rest state, wherein the elastically deformable element (130) is restricted to a gutter-shaped ring having a posterior lip (133b) which undulates in festoons.

9. An accommodating artificial lens device comprising an accommodating intraocular implant (100) comprising a single piece of elastically deformable material constituting a central lens (1) and at least two haptic portions (2, 4) in the form of radial arms, wherein a free end of each radial arm (2, 4) is fitted with a shoe (6, 7) of substantially toroidal outside surface, the connection between each shoe (6, 7) and the corresponding arm (2, 4) being of a hinge type situated in the vicinity of a posterior edge of the shoe (6, 7) and being formed by a first thin portion (2d, 4d) of the arm, while the connection between each said arm and the lens is of the hinge type implemented at an anterior surface of the lens by a second likewise thin portion (2c, 4c) of the arm, a plane ($P_1$) containing the first thin portions being situated behind a plane ($P_2$) containing the second thin portions, and including at least two rigid radial extensions (10, 12) extending from the lens (1) and interposed between pairs of the haptic arms, each extension being of radial length shorter than that of the arms, the accommodating artificial lens device further comprising an elastically deformable element (120, 130) separate from the implant, the element having at least a radially-deformable gutter-shaped peripheral portion whose diameter at a bottom of the gutter in a rest state is no greater than an outside diameter of the implant measured across outside faces of the shoe (110) when the implant is in the rest state.

10. A device according to claim 9, wherein the equatorial diameter of the separate element (120, 130) measured outside the gutter when in the rest state corresponds to the equatorial diameter that the capsular bag used to have when the patient for whom the device is intended was 20 to 30 years old.

11. A device according to claim 9, wherein the separate element (120) is in the form of a dome with a posterior web (125) having an edge in the form of a gutter.

12. A device according to claim 9, wherein the separate element (130) is restricted to a gutter-shaped ring having a posterior lip (133b) which undulates in festoons.

13. A device according to claim 9, wherein the gutter-shaped portion has a plurality of through slots (126, 136).

14. A device according to claim 9, wherein an anterior lip (122, 132) of the gutter-shaped portion has a radius smaller than the radial dimension of the rigid radial extensions of the implant.

15. A device according to claim 9, wherein the separate element (120, 130) has greater thickness (124, 134) at least in register with the end of each arm of the implant adjacent to its shoe, said extra thickness forming a posterior bearing abutment of the corresponding arm.

16. A device according to claim 9, including a third piece (150, 160) formed by a ring whose greatest diameter is no greater than the inside diameter of the gutter minus the thickness of the shoes of the arms of the implant as measured when the device is in its equilibrium state.

* * * * *